(12) United States Patent
Dalan et al.

(10) Patent No.: US 11,412,942 B2
(45) Date of Patent: Aug. 16, 2022

(54) APPARATUS, SYSTEM AND METHOD FOR OBTAINING HEMODYNAMIC DATA OF AN INDIVIDUAL

(71) Applicants: TAN TOCK SENG HOSPITAL PTE LTD, Singapore (SG); NANYANG POLYTECHNIC, Singapore (SG)

(72) Inventors: Rinkoo Dalan, Singapore (SG); Chee Teck Phua, Singapore (SG); Sieu Ley Goh, Singapore (SG)

(73) Assignees: Tan Tock Seng Hospital Pte Ltd, Singapore (SG); Nanyang Polytechnic, Singapore (SG)

( * ) Notice: Subject to any disclaimer, the term of this patent is extended or adjusted under 35 U.S.C. 154(b) by 285 days.

(21) Appl. No.: 16/480,310

(22) PCT Filed: Jan. 23, 2018

(86) PCT No.: PCT/SG2018/050041
§ 371 (c)(1),
(2) Date: Jul. 24, 2019

(87) PCT Pub. No.: WO2018/139973
PCT Pub. Date: Aug. 2, 2018

(65) Prior Publication Data
US 2020/0037898 A1 Feb. 6, 2020

(30) Foreign Application Priority Data
Jan. 24, 2017 (SG) .............................. 10201700605P

(51) Int. Cl.
*A61B 5/022* (2006.01)
*A61B 5/00* (2006.01)
*G06F 17/18* (2006.01)

(52) U.S. Cl.
CPC ........ *A61B 5/02233* (2013.01); *A61B 5/6824* (2013.01); *G06F 17/18* (2013.01); *A61B 2562/0247* (2013.01); *A61B 2562/04* (2013.01)

(58) Field of Classification Search
CPC ........ A61B 2562/04; A61B 2562/0247; A61B 5/6829; A61B 5/6828; A61B 5/6826;
(Continued)

(56) References Cited

U.S. PATENT DOCUMENTS 6,120,459 A 9/2000 Nitzan et al.
2004/0092832 A1* 5/2004 Schnall ................ A61B 5/6826
600/490

(Continued)

FOREIGN PATENT DOCUMENTS

WO 2002034105 A2 5/2002
WO 2008011079 A2 1/2008
WO 2013005179 A1 1/2013

OTHER PUBLICATIONS

Phua, C et al., 'Non-invasive Measurement of Blood Using Magnetic Disturbance Method', Published in 2009 International Conference on Biomedical and Pharmaceutical Engineering, IEEE, 2009, pp. 1-4. See whole document.

(Continued)

*Primary Examiner* — Tse W Chen
*Assistant Examiner* — Avery M Foley
(74) *Attorney, Agent, or Firm* — JCIP; Joseph G. Chu; Jeremy I. Maynard

(57) ABSTRACT

An apparatus, system and method for obtaining hemodynamic characteristics of an individual is disclosed. The apparatus comprises a first sensor arranged to sense a first hemodynamic data from a first radial artery; a second sensor arranged to sense a second hemodynamic data from a second radial artery; and an occlusion device arranged to be positioned around a third major blood vessel where the second major blood vessel branch from, the occlusion device operable to occlude the third major blood vessel for a predetermined period. The apparatus, system and method are suitable for deriving a risk indicator of one or more types of cardiovascular diseases.

8 Claims, 12 Drawing Sheets

(58) Field of Classification Search
CPC . A61B 5/6825; A61B 5/6824; A61B 5/02141;
A61B 5/021; A61B 5/0255; A61B 5/025;
A61B 5/02422; A61B 5/02405; A61B
5/024; A61B 5/023; A61B 5/0225; A61B
5/02225; A61B 5/02216; A61B 5/02208;
A61B 5/022; A61B 5/02241; A61B
5/02233; A61B 5/0265; G06F 17/18
See application file for complete search history.

(56) References Cited

U.S. PATENT DOCUMENTS

| | | | |
|---|---|---|---|
| 2005/0038345 A1* | 2/2005 | Gorgenberg | A61B 5/0205 600/485 |
| 2007/0276632 A1* | 11/2007 | Banet | A61B 5/0004 702/187 |
| 2008/0021334 A1* | 1/2008 | Finburgh | A61B 5/6833 600/490 |
| 2009/0264775 A1 | 10/2009 | Wu et al. | |
| 2017/0079533 A1* | 3/2017 | Robinson | A61B 5/0075 |
| 2018/0279965 A1* | 10/2018 | Pandit | A61B 5/7225 |

OTHER PUBLICATIONS

Phua Chee Teck, 'Novel method of blood pulse and flow measurement using the disturbance created by blood flowing through a localized magnetic field'. Other. Université Paris—Est. 2012. English. <NNT:2012PEST1099>. <tel-00794495>, Theses, HAL archieves-ouvertes.fr, Feb. 26, 2013, pp. 1-214 [retrieved from internet on Mar. 26, 2018]<URL: https:/tel.archives-ouvertes.fr/tel-00794495/document> see whole document.

Written opinion and ISR in International Application No. PCT/SG2018/050041. See whole document.

* cited by examiner

Legend:

SCORE – Systematic Coronary Risk Evaluation    UKPDS – UK Prospective Diabetes Study ADVANCE – ADVANCE Risk Assessment    HbA1c – Haemoglobin A1c H = Healthy    UH = Unhealthy

| Correlation Based on Actual Values | | Correlation Based on Classified Outcomes* | | *Classified Outcomes |
|---|---|---|---|---|
| RA-MDI-AVE vs | | IF(RA-MDI-AVE < CUTOFF, H, UH) (refer Pt-5 below) | | |
| SCORE | 0.4602 | SCORE | 0.5817 | If (SCORE > 0.9%, H, UH) |
| ADVANCE | 0.4631 | ADVANCE | 0.6022 | If (ADVANCE > 0.9%, H, UH) |
| UKPDS | 0.4674 | UKPDS | 0.7150 | If (UKPDS > 0.9%, H, UH) |
| HbA1c | 0.3820 | HbA1c | 0.7082 | If (Hba1C < 6.8, H, UH) |

| Correlation Based on Actual Values | | Correlation Based on Classified Outcomes* | | *Classified Outcomes |
|---|---|---|---|---|
| Competitor device vs | | IF(competitor device measument > 0.5128, H, UH) | | |
| SCORE | 0.094 | SCORE | 0.058 | If (SCORE > 0.9%, H, UH) |
| ADVANCE | 0.096 | ADVANCE | 0.074 | If (ADVANCE > 0.9%, H, UH) |
| UKPDS | 0.107 | UKPDS | 0.133 | If (UKPDS > 0.9%, H, UH) |
| HbA1c | 0.040 | HbA1c | 0.213 | If (Hba1C < 6.8, H, UH) |

FIG. 7

Linear regression analysis of the risk score, Carotid artery intima-media thickness and cardiovascular risk factors with the RA-MDI

| | Coef. | 95% Conf. Interval | | p-value |
|---|---|---|---|---|
| FHS_10 years Lipids (%) | 0.0292 | 0.0196 | 0.0387 | <0.001* |
| FHS_10 years BMI (%) | 0.0270 | 0.0187 | 0.0354 | <0.001* |
| FHS_30 years Lipids Full CVD(%) | 0.0102 | 0.0073 | 0.0131 | <0.001* |
| FHS_30 years Lipids Hard CVD (%) | 0.0124 | 0.0082 | 0.0166 | <0.001* |
| FHS_30 years BMI Full CVD (%) | 0.0097 | 0.0071 | 0.0123 | <0.001* |
| FHS _30 years BMI Hard CVD (%) | 0.0114 | 0.0081 | 0.0146 | <0.001* |
| SCORE (%) | 10.2713 | 4.0333 | 16.5092 | 0.002* |
| ADVANCE (%) | 9.6679 | 4.6630 | 14.6728 | <0.001* |
| UKPDS (%) | 1.6350 | 0.8316 | 2.4383 | <0.001* |
| Average CIMT | 1.6544 | 0.9372 | 2.3716 | <0.001* |
| Maximum CIMT | 0.9675 | 0.6110 | 1.3239 | <0.001* |
| Age (Years) | 0.0204 | 0.0145 | 0.0264 | <0.001* |
| Gender | | | | |
|   Male | Ref | | | |
|   Female | -0.2630 | -0.4741 | -0.0519 | 0.015* |
| Ethnicity | | | | |
|   Chinese | Ref | | | |
|   Malay | 0.0454 | -0.2604 | 0.3511 | 0.769 |
|   Indian | 0.3856 | 0.0662 | 0.7051 | 0.019 |
| BMI | 0.0252 | 0.0058 | 0.0446 | 0.012* |
| Systolic BP | 0.0118 | 0.0067 | 0.0170 | <0.001* |
| Diastolic BP | 0.0144 | 0.0057 | 0.0232 | 0.001* |
| Non-HDL | -0.0762 | -0.1778 | 0.0254 | 0.140 |
| LDL | -0.1074 | -0.1954 | -0.0194 | 0.017 |
| HbA1c | 0.1049 | 0.0611 | 0.1486 | <0.001* |
| Subject type | | | | |
|   Control | Ref | | | |
|   DM | 0.6174 | 0.4562 | 0.7786 | <0.001* |

FHS : Framingham risk scoring; CIMT: Carotid artery intima media thickness, p<0.01 is considered significant

FIG. 8b

Multivariable analysis looking at the correlation of RA-MDI with cardiovascular risk factors

|  | Coef. | 95% Conf. Interval | | p-value |
|---|---|---|---|---|
| Age (Years) | 0.0082 | -0.0014 | 0.0177 | 0.094* |
| Gender | | | | |
|   Male | Ref | | | |
|   Female | -0.1178 | -0.2813 | 0.0456 | 0.155 |
| BMI | -0.0038 | -0.0215 | 0.0140 | 0.676 |
| Systolic BP | 0.0001 | -0.0083 | 0.0085 | 0.985 |
| Diastolic BP | 0.0044 | -0.0065 | 0.0154 | 0.423 |
| LDL | 0.0102 | -0.0819 | 0.1023 | 0.826 |
| Subject type | | | | |
|   Control | Ref | | | |
|   DM | 0.3739 | 0.0704 | 0.6775 | 0.016* |

This is a multivariable regression model not stepwise model. If I use stepwise model, only DM would remain in the model.

FIG. 8c

APPARATUS, SYSTEM AND METHOD FOR OBTAINING HEMODYNAMIC DATA OF AN INDIVIDUAL

FIELD OF THE INVENTION

The invention relates to an apparatus, system and method for obtaining hemodynamic characteristic of an individual. In particular, the apparatus comprises a non-invasive platform for obtaining hemodynamic data to derive an indicator of cardiovascular diseases.

BACKGROUND ART

The following discussion of the background to the invention is intended to facilitate an understanding of the present invention only. It should be appreciated that the discussion is not an acknowledgement or admission that any of the material referred to was published, known or part of the common general knowledge of the person skilled in the art in any jurisdiction as at the priority date of the invention.

Existing apparatus for sensing or obtaining measurements relating to hemodynamic characteristics of an individual living subject may be either invasive or non-invasive. Non-invasive apparatus, for example ultrasonic sensors/scanners, while preferred from the patient's point of view to minimize discomfort, are often susceptible to noise and environmental disturbances, as well as inter or intra-operator variability as a result of the positioning on the living subject, such as varying angles and locations of the ultrasonic scanner when placed on the living subject.

Besides the type of apparatus, the method of obtaining hemodynamic measurements may also be a factor affecting quality and accuracy. In comparison to existing non-invasive method that uses micro-vascular sensors, clinicians had reported that the micro-vascular sensing method has a relatively higher dependency on environmental temperature.

Cardiovascular disease (CVD) is a major cause of mortality around the world. Studies have found that individuals with type 2 diabetes mellitus (T2DM) are more susceptible to CVD associated with coronary artery disease when compared to other non-diabetic individuals. Therefore there exists a constant need to identify and improve predictors of CVD and risk indicators for CVD.

Currently, clinical ways to assess cardiovascular risk include utilizing well-established cardiovascular metabolic risk factors or parameters such as glycemic control, lipids, body mass index (BMI), blood pressure, etc. Currently there are score matrix to derive the risk of different types of cardiovascular diseases, including the Framingham Risk Score (FRS), United Kingdom Prospective Diabetes Study (UKPDS) risk engine, Systematic Coronary Risk Evaluation (SCORE), and Action in Diabetes and Vascular Disease: Preterax and Diamicron-MR Controlled Evaluation (AD-VANCE) risk assessment. Typically if an individual has symptoms of coronary heart disease, a detailed coronary assessment is undertaken to identify whether the individual or patient suffers from significant ischemic heart disease. Such coronary assessment includes cardiac imaging using Myocardial Perfusion (MIBI) scan, treadmill ECG, coronary angiogram and coronary artery calcium scoring, amongst others. For peripheral vascular disease, peripheral circulation is assessed by measurements of toe brachial index, which are sensitive for significant ischemia in the tissue involved.

Despite the above ways to assess cardiovascular risks, there currently exists a need to provide a measure of endothelial dysfunction long before any ischemia symptoms can be measured or before the symptoms set in. Such early detection allows for appropriate intervention to be undertaken well in advance before clinically significant ischemic disease occurs. These risk scores use multiple clinical measurements (blood tests) and calculate the cardiovascular risk of one or more patients based on such multiple clinical measurements. In daily practice, such risk scores are rarely used by physicians because it requires a number of time consuming and expensive laboratory tests and the clinical performance may not be comprehensive.

Therefore, there exists a need for an improved apparatus and system to obtain or sense hemodynamic characteristics of an individual in a way that is more cost-effective and time efficient to minimizes inter-operator, intra-operator variability and/or intra patient variability. There also exists a need for an improved indicator for personalized quantification marker of cardiovascular disease, such as endothelial dysfunction.

It is an object of the invention to meet the aforementioned needs at least in part.

SUMMARY OF THE INVENTION

Throughout the specification, unless the context requires otherwise, the word "comprise" or variations such as "comprises" or "comprising", will be understood to imply the inclusion of a stated integer or group of integers but not the exclusion of any other integer or group of integers.

Furthermore, throughout the specification, unless the context requires otherwise, the word "include" or variations such as "includes" or "including", will be understood to imply the inclusion of a stated integer or group of integers but not the exclusion of any other integer or group of integers.

The apparatus is advantageous as it has the potential to be less affected by environmental conditions as it will measure the radial artery distensibility instead of peripheral capillaries.

According to an aspect of the invention there is an apparatus for obtaining hemodynamic characteristics of an individual comprising a first sensor arranged to sense a first hemodynamic data from a first major blood vessel; a second sensor arranged to sense a second hemodynamic data from a second major blood vessel; and an occlusion device arranged to be positioned around a third major blood vessel where the second major blood vessel branch from, the occlusion device operable to occlude the third major blood vessel for a predetermined period.

In some embodiments, the apparatus comprises at least one housing shaped and dimensioned to receive a portion of the individual and one of the first sensor or second sensor. In some embodiments, the housing comprises a rest for the portion of the individual to rest upon, and a latch for the first or second sensor to be embedded on, the rest and latch arranged such that a distance between the rest and the latch is adjustable to accommodate the portion of different sizes.

In some embodiments, the individual is a human being and the first and second major blood vessels are radial arteries of a right and left wrist of the human being respectively.

In some embodiments, the apparatus is integrated with a processor to store the first hemodynamic data and the second hemodynamic data.

In some embodiments, the occlusion device comprises a sphygmomanometer.

In some embodiments, the second hemodynamic data is obtained during a period of time before the occlusion state corresponding to a relaxation state and a period of time corresponding to a dilation state.

In some embodiments, the first hemodynamic data is obtained corresponding to the period of time when the second hemodynamic data is obtained.

In some embodiments, obtaining the second hemodynamic data further comprises detecting a peak corresponding to the maximum signal amplitude detected during the dilation state.

In some embodiments comprising the at least one housing, the apparatus further comprises at least one height adjustor for adjusting the distance between the rest and the latch.

In some embodiments, the first and/or the second major blood vessel is a radial artery.

In some embodiments, the third major blood vessel is a brachial artery.

In accordance with another aspect of the invention there is a system for deriving an indicator of one or more vascular diseases of an individual comprising a first sensor arranged to sense a first hemodynamic data obtained from a first major blood vessel; a second sensor arranged to sense a second hemodynamic data from a second major blood vessel; and an occlusion device arranged to be positioned around a third major blood vessel where the second major blood vessel branch from, the occlusion device operable to occlude the third major blood vessel for a predetermined period; and a processor operable to receive the first dataset and the second dataset for deriving the indicator of the one or more vascular diseases; wherein the first hemodynamic data and the second hemodynamic data are obtained before and after the predetermined period.

In some embodiments, the occlusion device comprises a sphygmomanometer.

In some embodiments, the second hemodynamic data is obtained during a period of time before the occlusion state corresponding to a relaxation state and a period of time after the occlusion state corresponding to a dilation state.

In some embodiments, the first hemodynamic data is obtained corresponding to the period of time when the second hemodynamic data is obtained.

In some embodiments, the indicator is derived based the first hemodynamic data, the second hemodynamic data, an age adjustment factor, a gender adjustment factor, a heart rate.

In some embodiments, the first and second major blood vessels are radial arteries on a living human subject's right and left wrists.

In some embodiments, the indicator (RA-MDI) is computed based on the following mathematical equation:

$$RA - MDI = \frac{\sum A / \sum B}{\sum C / \sum D} * \frac{AAdj * GAdj}{MAPn} * \frac{HR(R)}{HR(O)} * \frac{HR(D)}{HR(O)}$$

Where AAdj refers to an age adjustment factor to adjust for arterial dilation which degenerates with age; GAdj refers to a gender adjustment factor to adjust for difference in muscle structure across gender; HR(R) refers to heart rate obtained from the control wrist or arm during the relaxation period; HR(D) refers to heart rate during the dilation state; HR(O) refers to heart rate obtained during the occlusion state; $\Sigma A$, $\Sigma B$, $\Sigma C$, and $\Sigma D$ each refer to the summation of the hemodynamic data obtained for a predetermined period corresponding to the dilation state and relaxation state, wherein $\Sigma A$, $\Sigma B$ correspond to the hemodynamic data obtained on the occluded wrist during the dilation state and relaxation state respectively, and $\Sigma C$, $\Sigma D$ correspond to the hemodynamic data obtained on the control wrist during the dilation state and relaxation state respectively.

In some embodiments, there comprises a plurality of RA-MDI indicators derived and an average value RA-MDI-AVE is obtained. In some embodiments, if RA-MDI or RA-MDI-AVE is less than a cut-off value, the individual is classified as healthy, otherwise the individual is classified to suffer from a type of vascular disease known as endothelial dysfunction.

In some embodiments, the cut-off value is between 0.4 to 0.5.

According to another aspect of the invention there is a method for deriving an indicator of one or more vascular diseases of an individual comprising the steps of: occluding, using an occlusion device, a third major blood vessel for a predetermined period; obtaining from a first sensor, a first hemodynamic data from a first major blood vessel; and obtaining from a second sensor, a second hemodynamic data from the second major blood vessel; wherein the first hemodynamic data and the second hemodynamic data are obtained before and after the predetermined period, and the second major blood vessel branch from the third major blood vessel.

In some embodiments, the occlusion device comprises a sphygmomanometer.

In some embodiments, the step of obtaining the second hemodynamic data is during a period of time before the occlusion state corresponding to a relaxation state and a period of time after the occlusion state corresponding to a dilation state.

In some embodiments, the step of obtaining the first hemodynamic data correspond to the period of time when the second hemodynamic data is obtained.

In some embodiments, the indicator is derived based the first hemodynamic data, the second hemodynamic data, an age adjustment factor, a gender adjustment factor, a heart rate.

In some embodiments, the first and second major blood vessels are radial arteries on a living human subject's right and left wrists.

In some embodiments, the indicator (RA-MDI) is computed based on the following mathematical equation:

$$RA - MDI = \frac{\sum A / \sum B}{\sum C / \sum D} * \frac{AAdj * GAdj}{MAPn} * \frac{HR(R)}{HR(O)} * \frac{HR(D)}{HR(O)}$$

Where AAdj refers to an age adjustment factor to adjust for arterial dilation which degenerates with age; GAdj refers to a gender adjustment factor to adjust for difference in muscle structure across gender; HR(R) refers to heart rate obtained from the control wrist or arm during the relaxation period; HR(D) refers to heart rate during the dilation state; HR(O) refers to heart rate obtained during the occlusion state; $\Sigma A$, $\Sigma B$, $\Sigma C$, and $\Sigma D$ each refer to the summation of the hemodynamic data obtained for a predetermined period corresponding to the dilation state and relaxation state, wherein $\Sigma A$, $\Sigma B$ correspond to the hemodynamic data obtained on the occluded wrist during the dilation state and relaxation state respectively, and $\Sigma C$, $\Sigma D$ correspond to the hemodynamic data obtained on the control wrist during the dilation state and relaxation state respectively.

In some embodiments, there comprises a plurality of RA-MDI indicators derived and an average value RA-MDI-AVE is obtained.

In some embodiments, if RA-MDI or RA-MDI-AVE is less than a cut-off value, the individual is classified as healthy, otherwise the individual is classified to suffer from a type of vascular disease known as endothelial dysfunction.

In some embodiments, the cut-off value is between 0.4 to 0.5.

In accordance with another aspect of the invention there is a system for deriving an indicator of endothelial dysfunction of an individual comprising a first dataset comprising a first hemodynamic data obtained from a first major blood vessel; a second dataset comprising a second hemodynamic data obtained from a second major blood vessel; and a processor operable to receive the first dataset and the second dataset for deriving the indicator of endothelial dysfunction; wherein the first hemodynamic data and the second hemodynamic data are obtained before and after the occlusion of a third major blood vessel where the second major blood vessel branch from.

In accordance with another aspect of the invention there is a method for deriving an indicator of endothelial dysfunction of an individual comprising the steps of: occluding, using an occlusion device, a third major blood vessel for a predetermined period; obtaining a first hemodynamic data from a first major blood vessel; and obtaining a second hemodynamic data from a second major blood vessel; wherein the first hemodynamic data and the second hemodynamic data are obtained before and after the predetermined period and the second major blood vessel branch from the third major blood vessel.

BRIEF DESCRIPTION OF DRAWINGS

The present invention will be described, by way of example only, with reference to the accompanying drawings, in which:

FIG. 5 illustrates a stratification chart classifying individuals into healthy and unhealthy based on the method of FIG. 4a;

FIG. 7 are two tables showing the correlation between the RA-MDI and other CVD markers used to assess endothelial dysfunction;

FIGS. 8a to 8c illustrate data and results obtained in relation to a correlation study demonstrating the efficacy of the apparatus, system and/or method of various embodiments.

Other arrangements of the invention are possible and, consequently, the accompanying drawing is not to be understood as superseding the generality of the preceding description of the invention.

DESCRIPTION OF EMBODIMENTS OF THE INVENTION

The present invention may be understood more readily by reference to the following detailed description of certain embodiments of the invention.

Throughout the specification, where publications are referenced, the disclosures of these publications are hereby incorporated by reference, in their entireties, into this application in order to more fully describe the state of art to which this invention pertains.

In the description of various embodiments, details are set forth in order to provide a thorough understanding of the invention. However, it will be understood by those skilled in the relevant art that the present invention well-known methods, procedures, components, and materials may be practiced without these specific details.

In the description of various embodiments, the term 'major blood vessels' refer to arteries and veins.

In accordance with an aspect of the invention there comprises an apparatus 10 for acquiring or obtaining hemodynamic characteristics of an individual. The apparatus 10 comprises a first sensor 12 arranged to sense a first hemodynamic data from a first major blood vessel; a second sensor 14 arranged to sense a second hemodynamic data from a second major blood vessel; and a occlusion device 16 arranged to be positioned on or around a third major blood vessel where the second major blood vessel branch or continues from.

Figure 1A:
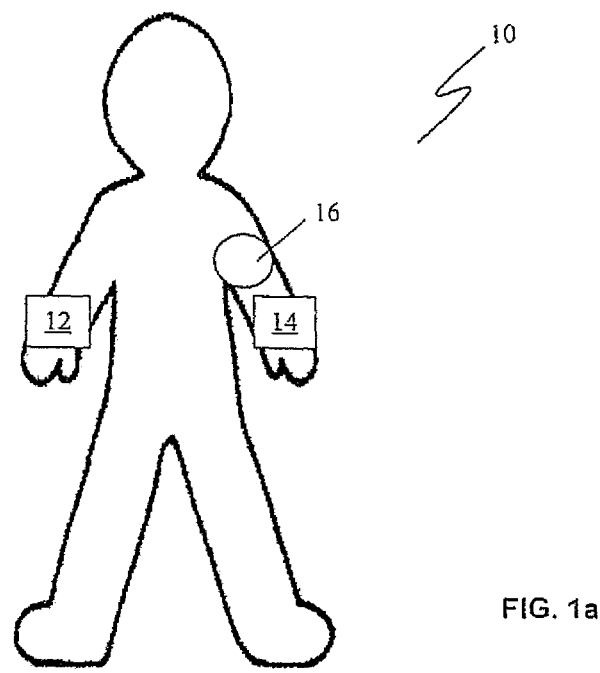
FIG. 1a illustrates an apparatus for obtaining hemodynamic data of a living subject.

The occlusion device 16 is operable to occlude the third major blood vessel for a predetermined period. Hemodynamic data or measurements are obtained via the first sensor 12 and second sensor 14 before and/or after the predetermined period. As illustrated in FIG. 1a, the first and second major blood vessels may be radial arteries on a left and a right hand of a living subject, and the third major blood vessel may be a brachial artery. In some embodiments, the occlusion device 16 may comprise a sphygmomanometer having an inflatable cuff. In some embodiments, the apparatus 10 is non-invasive, wherein the first and second sensors 12, 14 are non-invasive sensors.

Figure 1B:
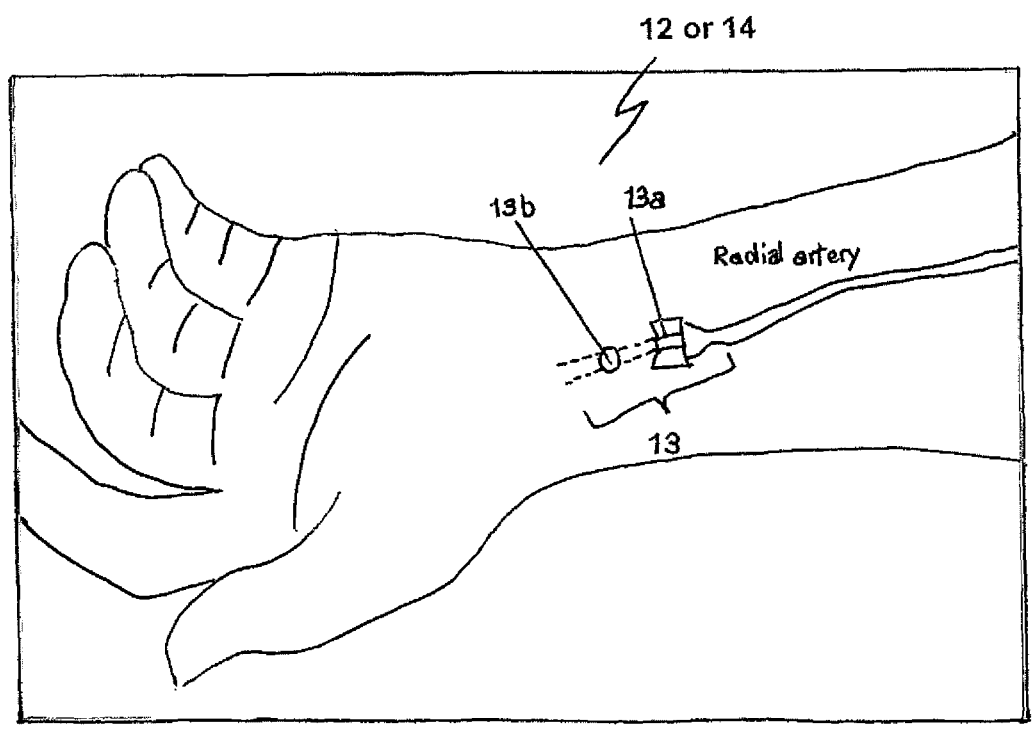
FIG. 1b illustrates a magnetic sensor arrangement according to some embodiments.

The individual is typically a living subject and in some embodiments is a living human being. FIG. 1b illustrates a magnetic sensor arrangement 13 that could be used as the first sensor 12, the second sensor 14 or both the first and second sensors 12, 14. The magnetic sensor arrangement 13 comprises a magnetic sensor 13a and magnet 13b, the magnetic sensor 13a and magnet 13b spaced apart by a predetermined distance for optimal sensor biasing and optimal magnetic coupling between the magnetic sensor 13a and magnet 13b. The predetermined distance may be between 1.0 centimeter and 1.3 centimeters.

In some embodiments, the magnetic sensor arrangement 13 may comprise a magnetic source for producing a localized, uni-directional, and constant magnetic field; and a signal acquisition module with a magnetic sensor, wherein the magnetic sensor is suitably positioned at, around, within or proximate the magnetic field to detect the modulation of the localized uni-directional and constant magnetic field caused by the effect on the blood flow on said magnetic field in a blood vessel near the skin surface of the living subject; a signal conditioning module for converting the output of the signal acquisition module with appropriate amplifications; and a digital signal processing module for processing the output signal from the signal conditioning module; thereby pulse rate and blood flow anomaly can be monitored. Such an arrangement is capable of acquiring hemodynamic data from radial arteries on the wrists of a living subject, in particular a human subject, in a synchronous manner, as described in U.S. Pat. No. 8,180,427 B2.

Figure 2A:
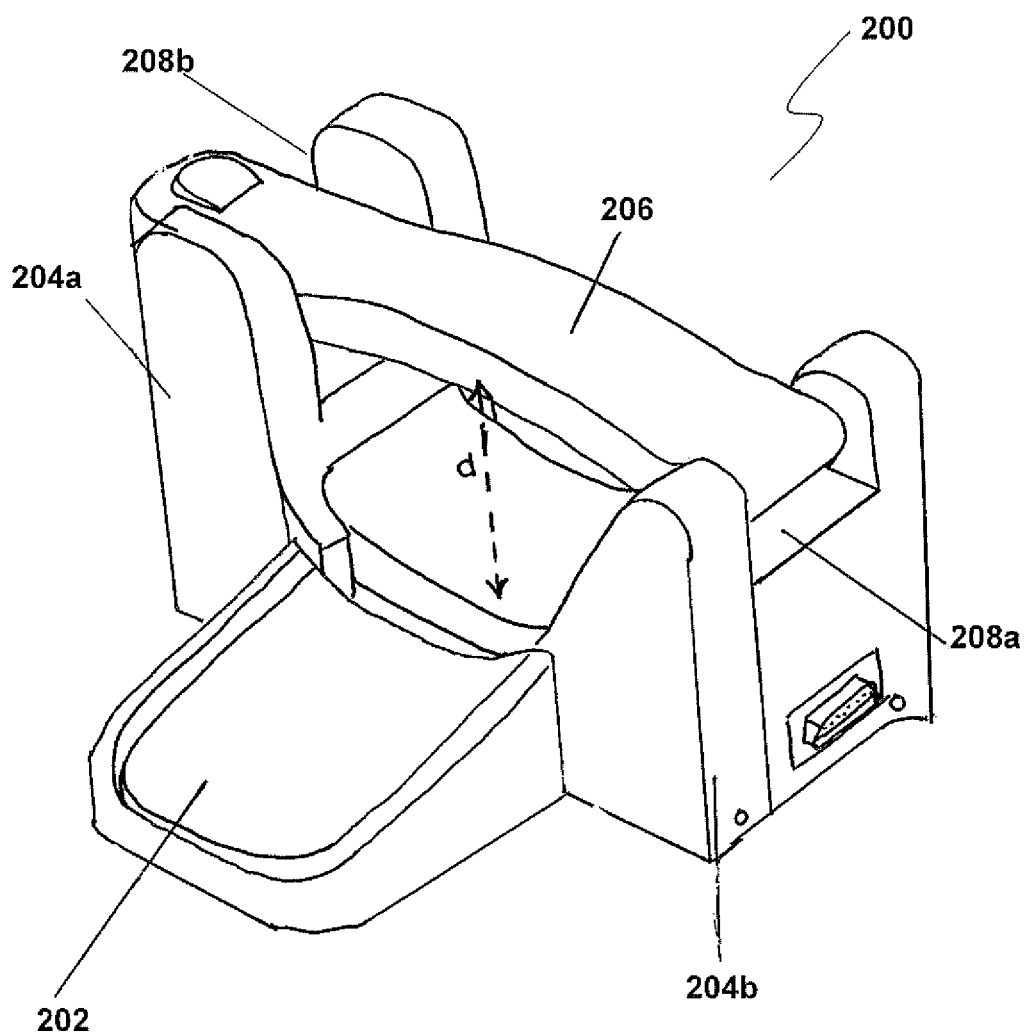
FIG. 2a illustrates a housing for containing a sensor arrangement, where the sensor arrangement comprises a magnetic sensor and magnet arrangement for acquiring or obtaining hemodynamic characteristics of an individual in some embodiments of the invention.

In an embodiment as illustrated in FIG. 2a, the first and/or second sensors are housed in a housing 200 having a rest 202, two vertical supports 204a and 204b, and a latch 206. The rest 202 is shaped and dimensioned to receive a body portion of a living subject, such as, but not limited to, a wrist, for the obtainment of hemodynamic data from the radial artery around the wrist region. One end of each of the two vertical supports 204a, 204b extends from opposing ends of the rest 202, while the other end of the two vertical supports 204a, 204b comprise corresponding indents 208a, 208b shaped to receive and hold the latch 206 at a distance d from a surface of the rest 202. The latch 206 is pivotable about the indent/hollow portion 208a while indent/hollow portion 208b is adapted for locking or securing the latch 206 in place once the latch 206 is received or positioned in the hollow portion 208b. The distance d may be adjusted or varied to suit wrists of differing size by varying the height of the supports 204a, 204b, or varying the height of the rest 202.

Figure 2B:
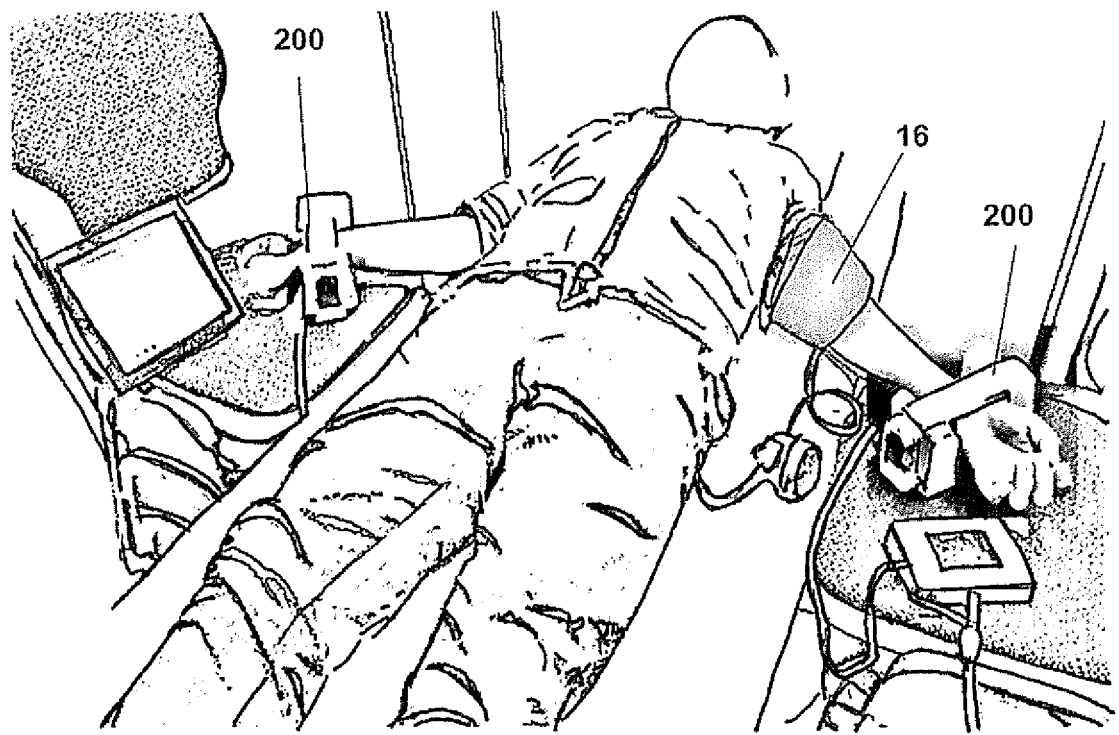
FIG. 2b illustrates some embodiments where an apparatus of FIG. 2a is attached to a human subject forming a system for obtaining hemodynamic characteristics of the human subject.
Figure 2C:
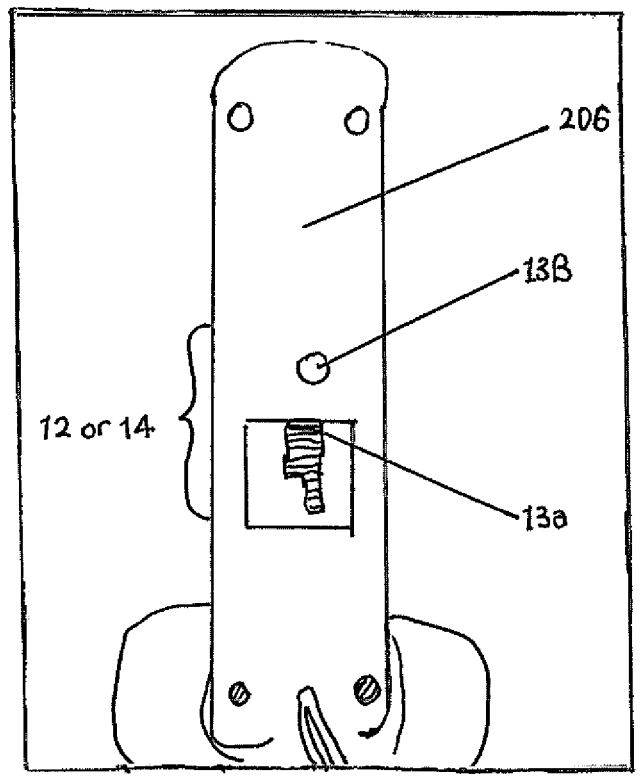
FIG. 2c is a close up view showing the positioning of magnetic sensor arrangement on a housing according to some embodiments of the apparatus.
Figure 3:
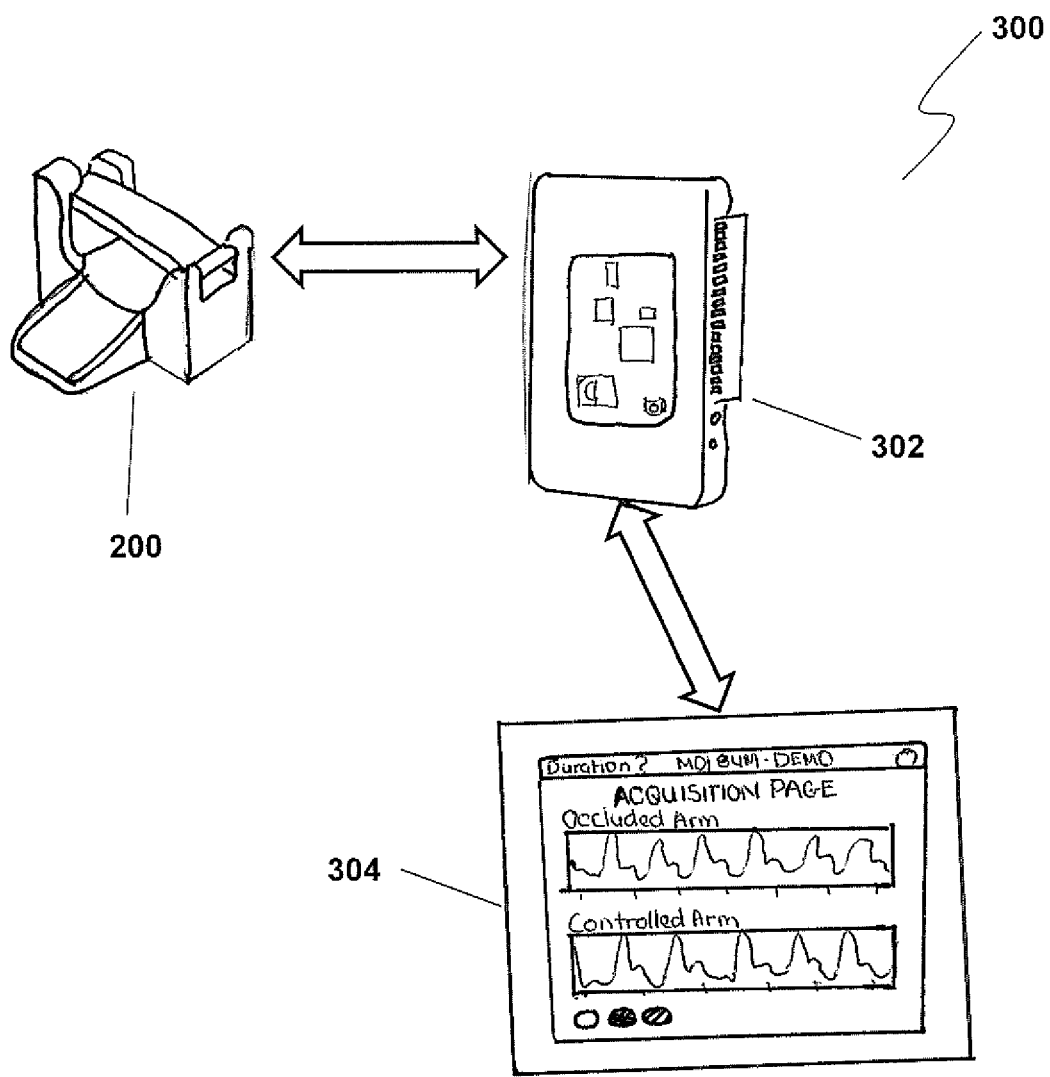
FIG. 3 illustrates a system diagram for acquiring or obtaining hemodynamic characteristics of an individual.

FIG. 2b shows an arrangement where the apparatus 10 is attached to a living human subject to form a system for obtaining hemodynamic data of the living human subject. Two housings 200 are attached to the left and right wrists of the human subject respectively. The first sensor 12 is embedded on the latch 206 (see FIG. 2c) of the right wrist, while the second sensor 14 is embedded on the latch 206 attached to the left wrist. The occlusion device 16 comprising the inflatable cuff, is wrapped around the brachial artery of the left arm. When properly positioned, the first sensor 12 and second sensor 14 are arranged proximate the respective radial artery as illustrated in FIG. 1 (without latch) for the obtainment of hemodynamic data. Hemodynamic data, which may be in the form of electronic signals such as pulses, are obtained from the radial arteries of both the left and right wrists with signals obtained from the right wrist as the control or reference data so as to minimize intra-patient variability.

In operation, the apparatus 10 is placed on the left and right wrists, and left arm of a living human subject such that:

a. on the left wrist, the second sensor 14 with the occlusion device 16 are used to acquire hemodynamic activities during baseline, occluded period and hyperemic period;

b. on the right wrist, the first sensor 12 is used to acquire the baseline hemodynamic activity of the cardiovascular system.

It is to be appreciated that the right arm serves as a reference (control) arm for sensing and acquiring subsequent hemodynamic data. Such an arrangement provides a reference point or a basis for reference to reduce or eliminate inter-operator and/or intra-operator variability.

In some embodiments, the latch 206 may comprises a deformable portion (not shown) wherein the sensor 12 or 14 may be embedded or attached onto. The deformable portion may comprise in part or wholly an airbag. Such an arrangement is advantageous in that depending on the height of the supports 204a and 204b, there exists a consistent and/or constant pressure exerted by contact of the sensor on the skin of the wrists to obtain the hemodynamic data.

In some embodiments, medical grade silicon slabs may be positioned on the rest 202 to adjust or increase the distance d between the rest 202 and the latch 206 so as to achieve proper contact with the sensors 12, 14 and enhance the quality of hemodynamic signal obtained.

The housing 200 is shaped such that the rest 202 and vertical supports 204 minimizes the movement of the respective wrist in position in order that the hemodynamic data, in the form of pulses, can be sensed by the respective sensors 12 and 14 once the latch 206 is secured.

In some embodiments, the housing 200 further comprises one or more electronic circuits that may be implemented within the housing 200. In some embodiments at least one of the electronic circuits may include one or more electrical and/or electronic components such as a signal amplifier, a noise cancellation/reduction module comprising one or more noise reduction components such as low pass, high pass or bandpass filters, signal conversion module such as analogue to digital and vice-versa. Such electronic circuits operate or function to ensure that the signals acquired are of an acceptable quality and is suitable for subsequent analysis. In alternative embodiments, the electronic circuits may be implemented in one or more separate devices or integrated in one or more processors arranged in data communication with the housing 200.

The apparatus 10 may form part of a non-invasive platform or system capable of acquiring hemodynamic characteristics on the macro-vascular system to assess risks of cardiovascular diseases (such as endothelial dysfunction) for patients with diabetes mellitus.

In another aspect of the invention there comprises a system 300 for obtaining hemodynamic data of an individual to derive an indication of endothelial dysfunction using the apparatus 10.

The system 300 comprises the apparatus 10 arranged with a processor 302 and a display interface 304. The apparatus 10, processor 302 and display interface and control unit 304 are arranged in data communication with one another. Such data communication may be based on known wired and wireless communication protocols and will not be elaborated further. Processor 302 may be an embedded device for data acquisition and analysis. The display interface is arranged in data communication with the processor 302 to display the analyzed results.

Figure 4A:
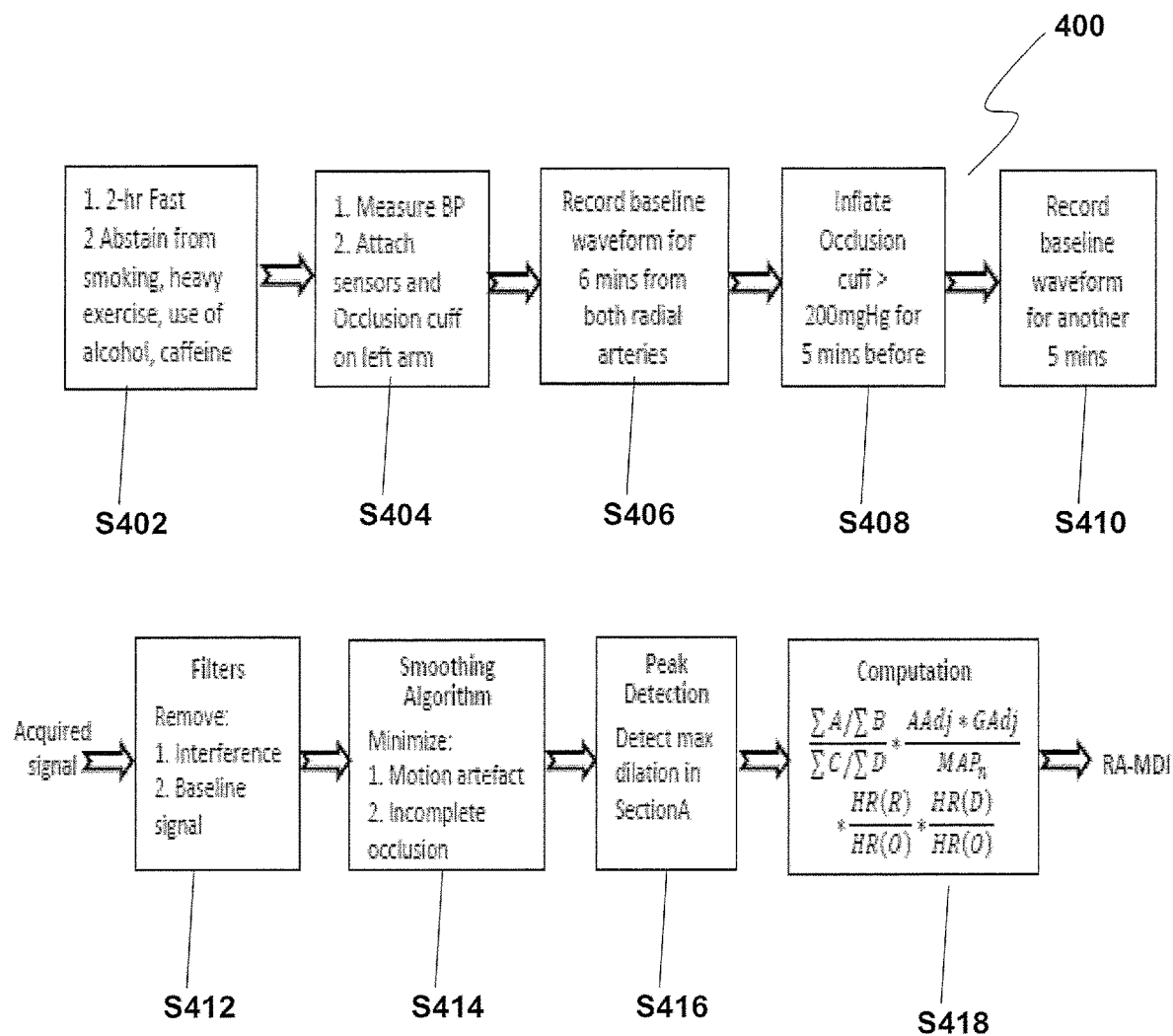
FIG. 4a illustrates a method for obtaining hemodynamic characteristics of an individual to derive an indication of endothelial dysfunction.

The operation of the apparatus 10, as an exemplary method 400 for obtaining hemodynamic signals/data of an living human subject to derive an indication of endothelial dysfunction, will be described with reference to FIG. 4a and FIG. 4b. The indication of endothelial dysfunction may be a personalized marker.

Prior to obtaining any measurement or hemodynamic data, there may comprise a pre-screening preparation step (step s402) which may include fasting for a predetermined period (e.g. 2 hours), abstinence from alcohol, smoking, heavy exercise, caffeine or any other activities that could possibly affect any of the measurements.

The apparatus 10 is then attached to the living subject as shown in FIG. 2b. Next the blood pressure of the living human subject is taken via a blood pressure measuring device (not shown) (step s404). The blood pressure measurement is obtained before any occlusion of the third major blood vessel, and before any hemodynamic data is obtained.

Hemodynamic data is then obtained from the left and right wrists' radial arteries for a predetermined period, such as six minutes (step s406) via both the first and second sensors 12, 14. The data obtained forms the baseline data corresponding to a relaxation period (B) and (D) shown in FIG. 4b.

The occlusion device 16 is next operated to an occluded state. If an inflatable pressure cuff is used as the occlusion device, the inflatable pressure cuff may be inflated to a pressure of more than 50 mm Hg of baseline systolic blood pressure with a maximum inflation pressure up to 250 mmHg for three to five minutes (step s408). In some embodiments, the inflatable pressure cuff is inflated to 200 mmHg to produce the necessary occlusion.

After the inflation, measurements are obtained from the first sensor 12 and second sensor 14 for about five minutes corresponding to a dilation state on the left arm and baseline on the right arm (step s410).

The acquired hemodynamic signals or data from the first sensor 12, second sensor 14 are then send to a noise reduction module (not shown) for filtering or removing any interference or noise. The baseline signal obtained from the control wrist (right wrist) is also filtered (step s412). The filtered signals or data are then passed to a smoothing algorithm to minimize motion artefact and incomplete occlusion (step s414). In particular, where the first and second sensors are magnetic sensors 13, the use of magnetic field sensing provides electrical isolation and is therefore less susceptible to body bioelectrical noise such as bioelectrical noise from the heart, brain and voluntary and involuntary motion artifacts. The smoothing algorithm may include calculation of moving average, filtering, and other well-known techniques as known to a skilled person.

Figure 4B:
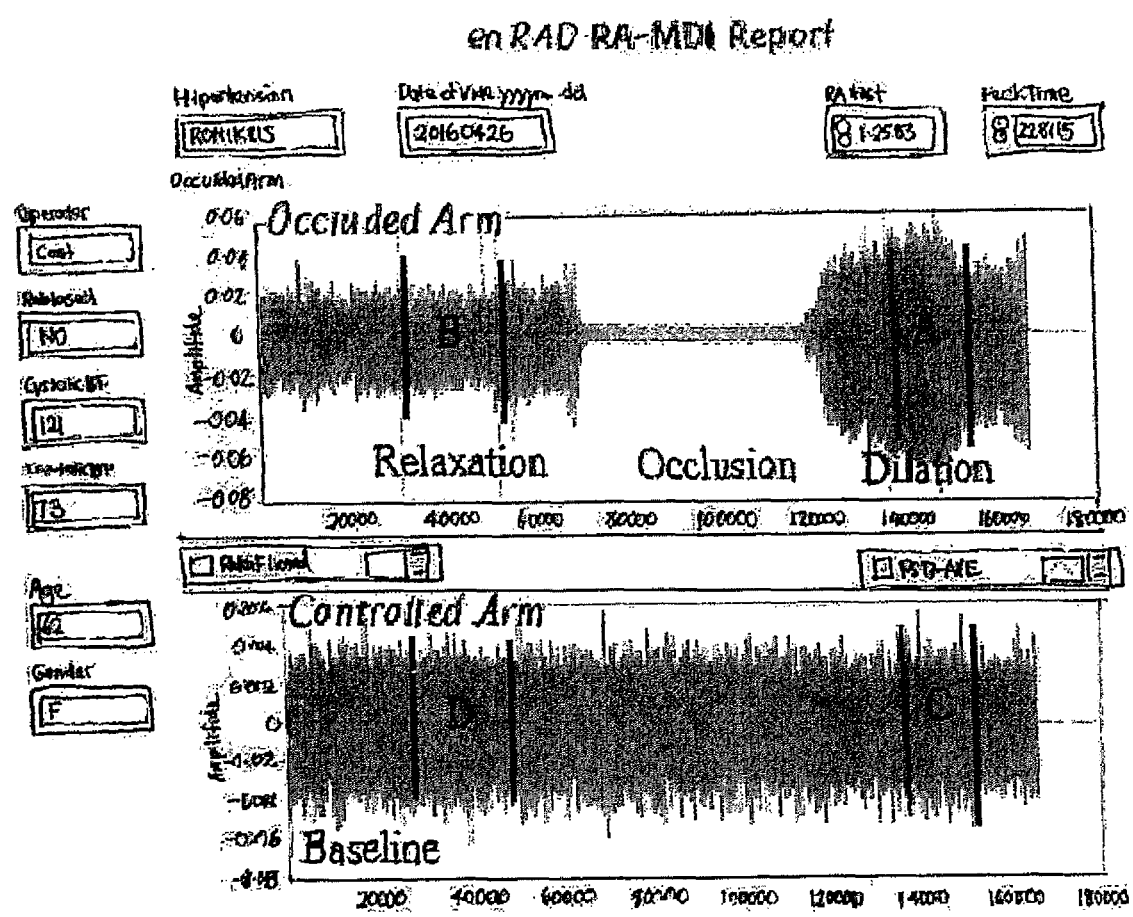
FIG. 4b illustrates examples of hemodynamic data obtained in the form of pulse waves.

In some embodiments, occlusion pressure is stopped when hemodynamic activities of the artery are minimally observable (i.e. less than 5% of the pulse amplitude during baseline measurements as shown in FIG. 4b).

After the minimization of motion artifacts and incomplete occlusion, the maximum signal amplitude corresponding to the dilation state (5 minutes) after the occlusion state is retrieved or computed from the data collected (step s416). An indicator of endothelial dysfunction, also referred to as a Radial Artery Maximum Distensibility Index (RA-MDI) is computed based on the following mathematical equation (step s418):

$$RA-MDI = \frac{\sum A / \sum B}{\sum C / \sum D} * \frac{AAdj * GAdj}{MAPn} * \frac{HR(R)}{HR(O)} * \frac{HR(D)}{HR(O)} \quad (1)$$

Where AAdj refers to an age adjustment factor to adjust for arterial dilation which degenerates with age; GAdj refers to a gender adjustment factor to adjust for difference in muscle structure across gender; HR(R) refers to heart rate obtained from the control wrist or arm during a relaxation period; HR(D) refers to heart rate obtained from the control wrist or arm during a dilation period; HR(O) refers to heart rate obtained from the control wrist or arm during a occlusion period; and $MAP_n$ refers to normalized mean arterial blood pressure. It is to be appreciated that the heart rate readings may be obtained from any arm as control arm.

The terms ΣA, ΣB, ΣC, and ΣD each refer to the summation of the signals obtained for a predetermined period during dilation and relaxation (on the occluded arm or wrist, i.e. ΣA, ΣB) and on the control arm or wrist (ΣC, ΣD) respectively.

From the hemodynamic data obtained, the pulse rate (corresponding to heart rate) can be calculated with the following mathematical equation:

$$\text{Pulse rate} = n \, T \times (60) \text{ pulses per minute} \quad (2)$$

where n is the number of pulses detected within the time duration T (in seconds); and T is the total time to observe n pulses.

Figure 5:
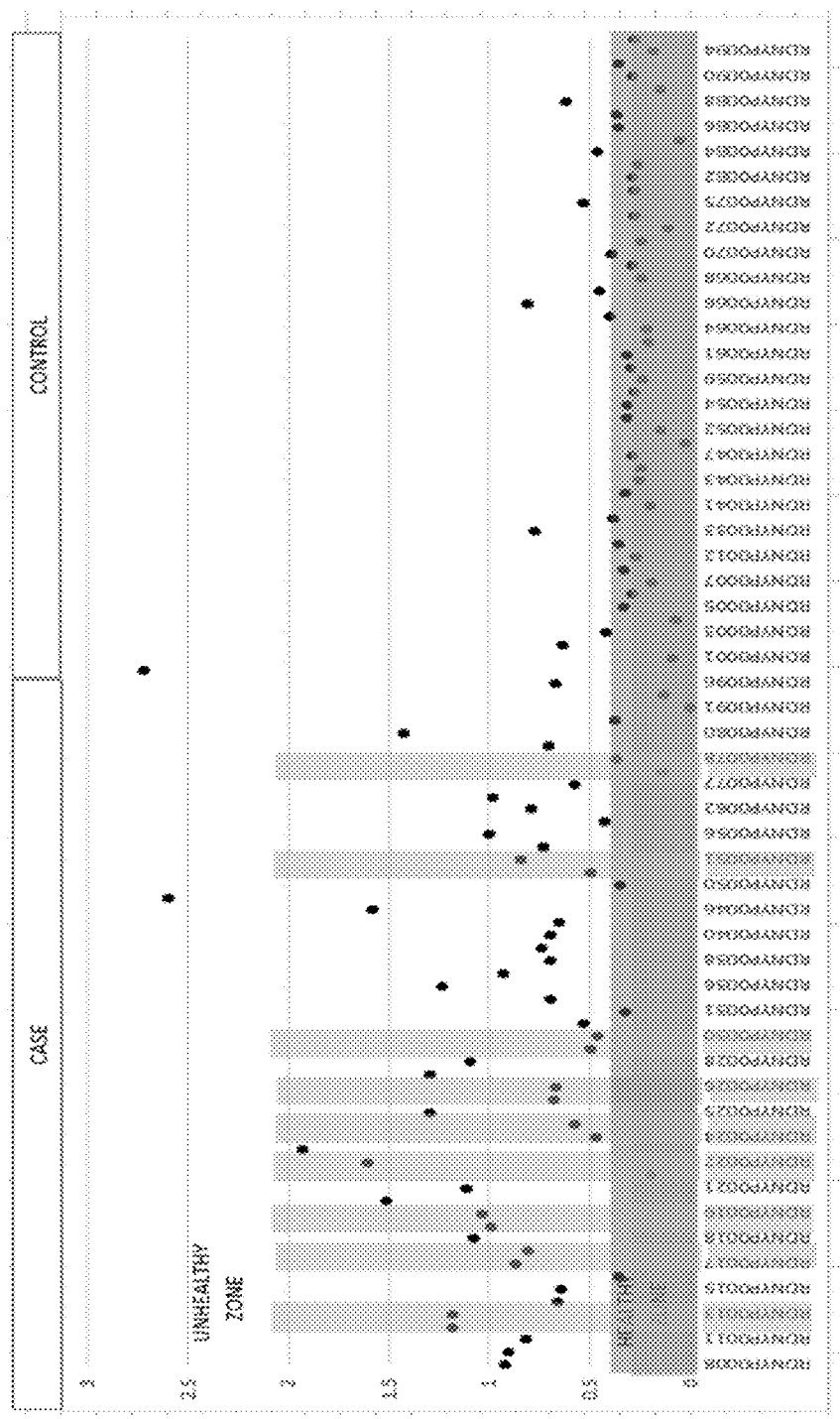

In some embodiments, the method 400 may be used to collected hemodynamic data from fifty (50) Diabetes Mellitus patients and fifty (50) healthy volunteers and comparisons made with traditional cardiovascular risk assessment tools using the UKPDS risk scores for patients and Framingham risk score for normal individuals. The obtained additional measurements form a dataset for further statistical parameters such as mean, median etc. to be calculated. The statistical parameters may be utilized to classify the healthy from the unhealthy living human subjects as shown in FIG. 5. From the classified data for the living subjects suffering from DM, it is apparent that the measurement and algorithm is consistent and repeatable. The overall results are also affirmative with an accuracy of 89.6% achieved.

Figure 6:
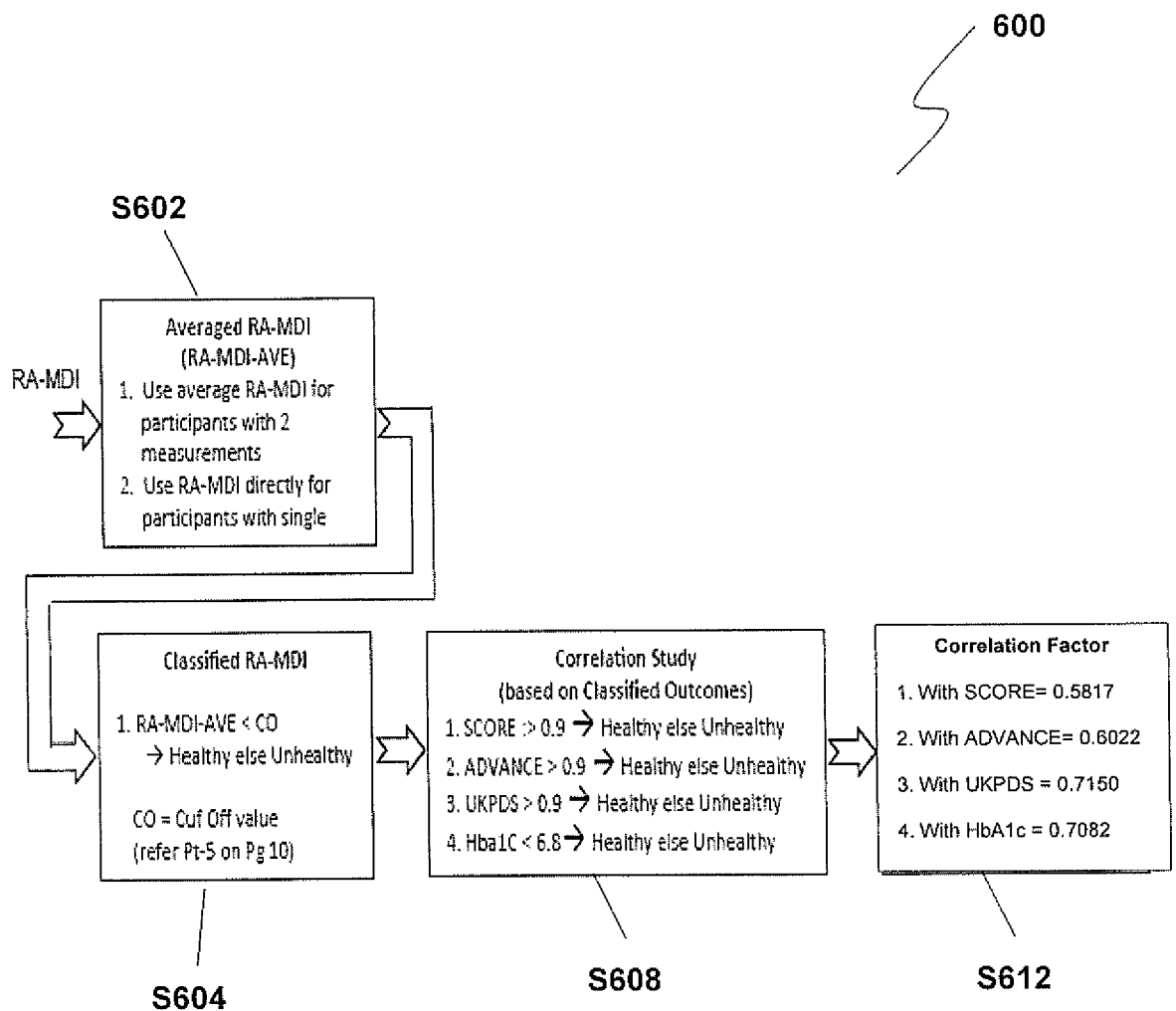
FIG. 6 is a flow chart showing the conduct of statistic analysis to assess the correlations between the indication of endothelial dysfunction (in the form of a quantification marker RA-MDI) against CVD risk scores.

FIG. 6 illustrates a method embodiment 600 for classifying whether a living subject can be classified as 'healthy' or 'not healthy'. The method comprises performing statistical analysis to assess correlations between the RA-MDI index derived for an individual against other conventional CVD risk scores such as SCORE, ADVANCE, UKPDS, HbA1C.

The method 400 is dependent on a cut-off value that is essential as a boundary value for classifying whether a living subject is deemed healthy or unhealthy. The measurements or data collected from the living subjects (whom are already known to be healthy or unhealthy) is used to derive the cut-off or boundary value. Through empirical evidence, the cut-off or boundary value is found to be within the range of 0.40 to 0.50. Preferably, the cut-off value is 0.45.

The method commences with step s602 wherein either a RA-MDI indicator or an average of a plurality of RA-MDI (hereinafter referred to as RA-MDI-AVE) indicators for an individual is obtained.

The RA-MDI or RA-MDI-AVE may be classified accordingly into either a 'healthy' group or an 'unhealthy' group according to the cut-off values and rules (step s604). Examples of such rules are as follows:

If RA-MDI or RA-MDI-AVE, as the case may be, is less than the cut-off value, the same is classified as healthy; otherwise, it is classified as unhealthy (step s604). It is to be appreciated that the cut-off value is different based on the different risk factors utilized.

The RA-MDI, and classified RA-MDI are correlated with the conventional score matrix (step s608). A respective correlation factor is derived thereafter (step s612). Referring to FIG. 7, correlation comparison studies performed between the derived RA-MDI, RA-MDI-AVE with the conventional score matrix, and an existing product showed that the RA-MDI, RA-MDI-AVE outperformed an existing product A. Existing product A involves the use of optical sensor which may not be suitable for obtaining measurements from major blood vessels such as arteries, and can only be used in minor blood vessels such as capillaries.

Further Correlation Study

Figure 8A:
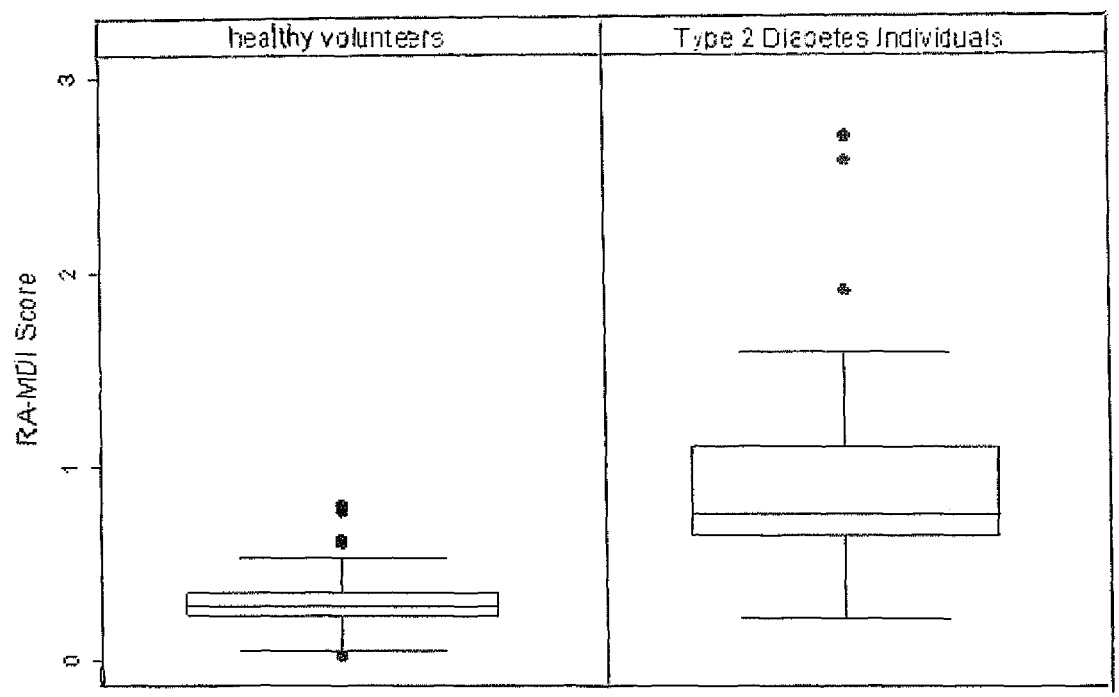

The efficacy of the apparatus, system and method were further established via a correlation study, the results of which is illustrated in FIGS. 8a, 8b and 8c. With arterial waveforms obtained using the apparatus, the mathematical equations (1) and (2) were used to quantify maximum possible dilation of the blood vessel(s). The baseline arterial waveforms from both hands were compared to arterial waveforms obtained after a period of occlusion for five (5) minutes in the occluded arm to determine the radial artery maximum distensibility index (RA-MDI).

Ninety-six (96) subjects consisting of 46 subjects with T2DM and 50 healthy subjects were studied. Correlations between RA-MDI indices with cardiovascular risk factors, scoring systems, and to carotid-artery-intima-media thickness (CIMT) were obtained.

FIG. 8a shows box plots plotted for the healthy subjects and the subjects with T2DM. Referring to FIG. 8a, it is shown that the RA-MDI scores were significantly higher in subjects with T2DM (Median 0.76, inter-quartile range IQR: 0.46) compared to healthy individuals (Median: 0.28, IQR: 0.13); $p<0.001$.

In FIG. 8b, a linear regression analysis (where $\beta$ is the coefficient of correlation and p is the null hypothesis, where $p<0.001$) showed RA-MDI scores correlated with other risk scoring systems comprising a. Framingham Heart Study (lipids full CVD 30 years): $\beta=0.01$ (95% confidence interval CI: 0.01-0.01);

b. UKPDS: $\beta=1.6$ (95% CI: 0.8-2.4);

c. ADVANCE: $\beta=9.67$ (95% CI: 4.66-14.67); and d. CIMT: $\beta=0.97$ (95% CI: 0.61-1.32).

In the correlation with other cardiovascular risk factors, it was noted that for glycated hemoglobin (HbA1c) $\beta=0.10$ (95% CI: 0.06-0.15);

Age $\beta=0.02$ (95% CI: 0.01-0.03);

systolic blood pressure $\beta=0.01$ (95% CI: 0.01-0.01);

diastolic BP $\beta=0.01$ (95% CI: 0.01-0.02); and

BMI $\beta=0.03$ (95% CI: 0.01-0.04), $p=0.01$.

With the analysis, it was found that the RA-MDI correlated significantly with traditional cardiovascular risk factors, scoring systems and CIMT.

Non-exhaustive advantages of the apparatus, system and method for obtaining hemodynamic data of an individual are highlighted as follows:

i. Hemodynamic data are acquired or obtained from one or more radial arteries. This is distal compared to brachial artery and is a better indicator for individuals with diabetes where peripheral small vessels are affected. It also has the advantage of less interference from the environment.

ii. Hemodynamic data are acquired from both wrists with one wrist being a reference (control arm) while data acquisition from the other wrist comprises the application of an appropriate level of occlusion on the other arm to achieve minimum arterial flow for a specific period to observe the change in blood flow characteristics. By having a reference, intra-patient variability is minimized.

iii. The method 400 is used for generation of a personalized quantification marker of cardiovascular disease, such as endothelial dysfunction, from the macro-vascular activities measured from each individual. Adjustments for signal noise caused by incomplete occlusion that may occur due to the physique of the different individuals is taken into account. Through the method 600 for classifying and correlation, the method 400 is proven to be able to achieve higher correlation to the macro-vascular endothelial function and hence lower intra-patient variability as it includes a basis point for reference (control arm) during computation.

The provision of a personalized marker in the form of RA-MDI enables skilled practitioners such as clinicians to assess endothelial function which is an assessment of the risk of development of vascular problems, diabetes and its associated vascular complications. It also enables the clinicians to assess the efficacy of specific medical treatment through quantitative measurements of the vascular activities.

The described apparatus, system and method can be used by clinicians to monitor hemodynamic activities of vascular system for all patients at risk of vascular problems such as, but not limited to, diabetes mellitus, hypertension and hyperlipidemia. Based on monitored results, clinicians will be able to stratify the severity of the vascular abnormality and identify individuals for appropriate medical treatment where applicable. Efficacy of treatment and drug effectiveness may be easily monitored using the apparatus and system. The ease of use and relatively high accuracy due to its independence between different operators and individuals may enhance the use of such apparatus and system in clinics or other health care institutions for monitoring and controlling chronic diseases such as diabetes mellitus, hypertension and hyperlipidemia on the vascular/endothelial function.

The apparatus and system can also be utilized as a research tool to evaluate the effects of various interventions on vascular risk in the short term. The apparatus and system can also be used by individuals such as patients and their healthcare providers as a lifestyle product.

The above is a description of embodiments of apparatus, systems and methods in accordance with the present invention. It is envisioned that those skilled in the art can design alternative embodiments of this invention that falls within the scope of the invention. In particular, It is envisaged that the major blood vessels may include arteries such as femoral artery, popliteal artery, proximal artery, and tibial artery.

Different types of sensors, whether invasive or non-invasive, capable of detecting and obtaining hemodynamic characteristics data may be utilized for the first sensor 12 and/or second sensor 14.

Although the embodiments have been described with reference to left and right arms of a living human subject, it is to be appreciated that the positioning of the occlusion device 16 can be on a dominant arm (i.e. either left or right) of the living human subject.

It is envisaged that the apparatus and system as described in the embodiments may be deployed in any living subjects having first, second, and third major blood vessels such as mammals.

In addition to providing an indicator of endothelial dysfunction, it is envisaged that the apparatus and system may be used to derive an indicator of one or more vascular diseases such as arterial distensibility (stiffness) and/or peripheral resistance of arteries in an individual.

Further, it is to be appreciated that element(s) in one embodiment, not being alternative to element(s) in another embodiment, may be combined to form yet other embodiments. It should also be appreciated by the person skilled in the art that variations and combinations of features described above, not being alternatives or substitutes, may be combined to form yet further embodiments falling within the intended scope of the invention.

The invention claimed is:

1. A system for deriving an indicator of one or more vascular functions of an individual comprising
   a first sensor arrangement comprising a first magnetic sensor and a first magnet embedded or attached to a deformable portion arranged to sense a first hemodynamic data obtained from a first radial artery, the first sensor arrangement housed in a housing dimensioned to receive a right wrist;
   a second sensor arrangement comprising a second magnetic sensor and a second magnet embedded or attached to a deformable portion arranged to sense a second hemodynamic data from a second radial artery, the second sensor arrangement housed in a housing dimensioned to receive a left wrist;
   an occlusion device arranged to be positioned around a third major blood vessel where the second radial artery branch from, the occlusion device operable to occlude the third major blood vessel for a predetermined period; and
   a processor operable to receive the first hemodynamic data and the second hemodynamic data for deriving the indicator of the one or more vascular functions; wherein the first hemodynamic data and the second hemodynamic data are obtained before and after the predetermined period, wherein the indicator is derived based on the first hemodynamic data, the second hemodynamic data, an age adjustment factor, a gender adjustment factor, and a heart rate, wherein the indicator (RA-MDI) is computed based on the following mathematical equation:

$$RA-MDI = \frac{\sum A / \sum B}{\sum C / \sum D} * \frac{AAdj * GAdj}{MAPn} * \frac{HR(R)}{HR(O)} * \frac{HR(D)}{HR(O)}$$

where AAdj refers to the age adjustment factor to adjust for arterial dilation which degenerates with age; GAdj refers to the gender adjustment factor to adjust for difference in muscle structure across gender; HR(R) refers to heart rate obtained from a control wrist during a relaxation period; HR(D) refers to heart rate during a dilation state; HR(O) refers to heart rate obtained during an occlusion state; ΣA, ΣB, ΣC, and ΣD each refer to a summation of a hemodynamic data obtained for a predetermined period corresponding to the dilation state and relaxation state, wherein ΣA, ΣB correspond to a hemodynamic data obtained on the occluded wrist during the dilation state and relaxation state respectively, and ΣC, ΣD correspond to a hemodynamic data obtained on the control wrist during the dilation state and relaxation state respectively.

2. The system according to claim 1, wherein there comprises a plurality of RA-MDI indicators derived and an average value RA-MDI-AVE is obtained.

3. The system according to claim 2, wherein if the RA-MDI or the RA-MDI-AVE is less than a cut-off value, the individual is classified as healthy, otherwise the individual is classified to suffer from an endothelial dysfunction.

4. The system according to claim 3, wherein the cut-off value is between 0.4 to 0.5.

5. A method for deriving an indicator of one or more vascular functions of an individual comprising the steps of:
   occluding, using an occlusion device, a third major blood vessel for a predetermined period;
   adjusting a first sensor arrangement comprising a first magnetic sensor and a first magnet embedded or attached to a deformable portion to exert a consistent and/or constant pressure on a first radial artery;
   obtaining from the first sensor arrangement, a first hemodynamic data from the first radial artery;
   adjusting a second sensor arrangement comprising a second magnetic sensor and a second magnet embedded or attached to a deformable portion to exert a consistent and/or constant pressure on a second radial artery; and
   obtaining from the second sensor arrangement, a second hemodynamic data from the second radial artery;
   wherein the first hemodynamic data and the second hemodynamic data are obtained before and after the predetermined period, and the second radial artery branch from the third major blood vessel, wherein the indicator is derived based on the first hemodynamic data, the second hemodynamic data, an age adjustment factor, a gender adjustment factor, a heart rate, wherein the indicator (RA-MDI) is computed based on the following mathematical equation:

$$RA-MDI = \frac{\sum A / \sum B}{\sum C / \sum D} * \frac{AAdj * GAdj}{MAPn} * \frac{HR(R)}{HR(O)} * \frac{HR(D)}{HR(O)}$$

where AAdj refers to the age adjustment factor to adjust for arterial dilation which degenerates with age; GAdj refers to the gender adjustment factor to adjust for difference in muscle structure across gender; HR(R) refers to heart rate obtained from a control wrist during a relaxation period; HR(D) refers to heart rate during a dilation state; HR(O) refers to heart rate obtained during an occlusion state; ΣA, ΣB, ΣC, and ΣD each refer to a summation of a hemodynamic dataset obtained for a predetermined period corresponding to the dilation state and relaxation state, wherein ΣA, ΣB correspond to a hemodynamic data obtained on the occluded wrist during the dilation state and relaxation state respectively, and ΣC, ΣD correspond to a hemodynamic data obtained on the control wrist during the dilation state and relaxation state respectively.

6. The method according to claim 5, wherein there comprises a plurality of RA-MDI indicators derived and an average value RA-MDI-AVE is obtained.

7. The method according to claim 6, wherein if the RA-MDI or the RA-MDI-AVE is less than a cut-off value, the individual is classified as healthy, otherwise the individual is classified to suffer from an endothelial dysfunction.

8. The method according to claim 7, wherein the cut-off value is between 0.4 to 0.5.

* * * * *